United States Patent [19]

Aramori et al.

[11] Patent Number: 5,310,659
[45] Date of Patent: May 10, 1994

[54] GL-7ACA ACYLASE

[75] Inventors: Ichiro Aramori, Kyoto; Masao Fukagawa, Tsuchiura; Hiroki Ono, Osaka; Yosuke Ishitani, Kobe; Mana Tsumura; Morita Iwami, both of Tsukuba; Hitoshi Kojo, Tsuchiura, all of Japan

[73] Assignee: Fujisawa Pharmaceutical Co., Ltd., Osaka, Japan

[21] Appl. No.: 779,049

[22] Filed: Oct. 18, 1991

[30] Foreign Application Priority Data

Oct. 22, 1990 [GB] United Kingdom ................ 9022907

[51] Int. Cl.$^5$ .......................... C12P 39/00; C12N 9/80
[52] U.S. Cl. ........................................ 435/43; 435/228
[58] Field of Search .................. 435/228, 227, 229, 43

[56] References Cited

U.S. PATENT DOCUMENTS 3,821,081 6/1974 Abe et al. ............................ 435/228

OTHER PUBLICATIONS

Yuzo Shibuya et al "Isolation and Properties of 7-Beta-(4-Carboxybutanamido)Cephalosporanic Acid Acylase-Producing Bacteria," Agric. Biol. Chem., 45(7), 1561-1567 (1981).
Dr. Tadashiro Fujii et al, "Enzymatic Synthesis of Cephalexin," Process Biochemistry, pp. 21-24 (1976).
Journal of Bacteriology, vol. 163, No. 3, Sep. 1985, pp. 1222-1228, A. Matsuda, et al., "Molecular Cloning and Structure of the Gene for 7-Beta-(4-Carboxybutanamido) Cephalosporanic Acid Acylase from a Pseudomonas Strain".
Journal of Bacteriology, vol. 169, Dec. 1987, pp. 5815-5820, A. Matsuda, et al., "Cloning and Characterization of the Genes for Two Distinct Cephalosporin Acylases from a Pseydomonas Strain".
Journal of Bacteriology, vol. 169, Dec. 1987, pp. 5821-5826, A. Matsuda, et al., "Nucleotide Sequences of the Genes for Two Distinct Cephalosporin Acylases from a Pseudomonas Strain".
Patent Abstracts of Japan, vol. 9, No. 254, (C-308)(1977), Oct. 11, 1985, & JP-A-60 110 292, Jun. 15, 1985, K. Komatsu, et al., "DNA Fragment Carrying Cephalosporin Acylase Production Gene Information".
Journal of Fermentation and Bioengineering, vol. 72, No. 4, pp. 227-231, 1991, I. Aramori, et al., "Isolation of Soil Strains Producing New Cephalosporin Acylases".

*Primary Examiner*—Robert A. Wax
*Assistant Examiner*—D. Schmickel
*Attorney, Agent, or Firm*—Oblon, Spivak, McClelland, Maier & Neustadt

[57] ABSTRACT

A GL-7ACA acylase having the following characteristics:
(a) has ability to catalyze the enzymatic conversion of glutaryl 7-ACA, adipyl 7-ACA, and succinyl 7-ACA, into 7-aminocephalosporanic acid,
(b) has a molecular weight of 70,000 dalton (SDS-PAGE) and
(c) has N-terminal amino acid sequence (SEQ ID NO: 1) thereof: Gln-Ser-Glu-Gln-Glu-Lys-Ala-Glu-Glu-.

A process for producing GL-7ACA acylase is also provided.

4 Claims, 9 Drawing Sheets

```
TCACATTGAC AGTTAAGCAA TTTTTATTAA ATATTACATA CCAACTTCCA CATATATCAA      60
TAAGGTTTAT ACTTTATTGA TATAGCAACT ATAATAATCC AACTAAATAC CTATATCCTT     120
TTTCCCGCGA ATGTCCTATT TACTTATTTT TCCTATCGAT ATAATATTAG TTTGAAAATT     180
TTAAAAATAA AGAAAATGGA GGTGTGTGC ATG AAT AGA AAG AAA AAA TTT CTT       233
                                Met Asn Arg Lys Lys Lys Phe Leu
                                -27     -25                 -20

TCT ATG CTG CTG ACT GTT CTT TTA GTC ACA TCA TTA TTT AGC AGT GTG       281
Ser Met Leu Leu Thr Val Leu Leu Val Thr Ser Leu Phe Ser Ser Val
            -15             -10                 -5

GCT TTT GGG CAG TCA GAG CAG GAA AAG GCA GAA GAA CTT TAT CAG TAT       329
Ala Phe Gly Gln Ser Glu Gln Glu Lys Ala Glu Glu Leu Tyr Gln Tyr
             1               5                  10

GAA CTT AAG ACT GAC GTT ATG GTA GAA ATG CGC GAT GGT GTA AAA CTG       377
Glu Leu Lys Thr Asp Val Met Val Glu Met Arg Asp Gly Val Lys Leu
         15              20              25

GCT ACA GAT ATT TAC CTG CCG GTT GCC AAA ACG GAG CAA GAA AAG AAA       425
Ala Thr Asp Ile Tyr Leu Pro Val Ala Lys Thr Glu Gln Glu Lys Lys
         30              35              40              45

GAT GGT TTT CCT ACG CTT GTG TTT CGA ACT CCT TAC AAC AAG GAT ACA       473
Asp Gly Phe Pro Thr Leu Val Phe Arg Thr Pro Tyr Asn Lys Asp Thr
             50              55              60

TAT GGG AAA ACT GAA GGT CCT TTC TTT GCA AAA AGA GGC TAT GCA GTG       521
Tyr Gly Lys Thr Glu Gly Pro Phe Phe Ala Lys Arg Gly Tyr Ala Val
             65              70              75

GTT GTT CAG GAT ACA CGT GGC CGC TAC AAG TCA GAA GGA GAA TGG AAC       569
Val Val Gln Asp Thr Arg Gly Arg Tyr Lys Ser Glu Gly Glu Trp Asn
         80              85              90

TTT GTA TTT GAT GAT GCC AAG GAT GGC TAT GAT TTA ATT GAA TGG GCT       617
Phe Val Phe Asp Asp Ala Lys Asp Gly Tyr Asp Leu Ile Glu Trp Ala
         95              100             105

GCA GTT CAG GAT TTC AGT ACT GGG AAG GTT GGC ACA ATG GGC CTA TCT       665
Ala Val Gln Asp Phe Ser Thr Gly Lys Val Gly Thr Met Gly Leu Ser
110             115             120             125

TAC ATG GCC TAT ACC CAG TAT GTA TTG GCT GAA TCA AAA CCG CCT CAT       713
Tyr Met Ala Tyr Thr Gln Tyr Val Leu Ala Glu Ser Lys Pro Pro His
            130             135             140
```

FIG. 4-1

| | | |
|---|---|---|
| CTT GTT ACA ATG ATT CCG CTT GAA GGG ATG AGC AAT CCT GCT GAA GAA | 761 | |
| Leu Val Thr Met Ile Pro Leu Glu Gly Met Ser Asn Pro Ala Glu Glu | | |
|            145           150           155 | | |

```
CTT GTT ACA ATG ATT CCG CTT GAA GGG ATG AGC AAT CCT GCT GAA GAA     761
Leu Val Thr Met Ile Pro Leu Glu Gly Met Ser Asn Pro Ala Glu Glu
            145             150             155
GTC TTT TTT ACA GGC GGA GCT ATG CAG CTA GAC CGC TAT TTA TCA TGG     809
Val Phe Phe Thr Gly Gly Ala Met Gln Leu Asp Arg Tyr Leu Ser Trp
            160             165             170
ACT TTG GGC CAG GCG GTA GAT ACA GCA AGA CGA CTT GAC GAA AAG AAT     857
Thr Leu Gly Gln Ala Val Asp Thr Ala Arg Arg Leu Asp Glu Lys Asn
            175             180             185
GGA AAT ACT GTT AAC CAG GAT AAG ATT AAA AAA GCG TTA GAT GAT TAT     905
Gly Asn Thr Val Asn Gln Asp Lys Ile Lys Lys Ala Leu Asp Asp Tyr
190             195             200             205
GAG AAG TGG CTT AAT CAT ATG CCA AGA TCT AAG GTG GCA CCA TTA AAC     953
Glu Lys Trp Leu Asn His Met Pro Arg Ser Lys Val Ala Pro Leu Asn
            210             215             220
CAA ATG ATT GAT TGG TGG AAA GAA GCG ATG GAT CAT CCT GAG TAT GAC    1001
Gln Met Ile Asp Trp Trp Lys Glu Ala Met Asp His Pro Glu Tyr Asp
            225             230             235
GAG TAT TGG AAG AGC ATC TCT CCT CAG GAA CAA CAT GAT ACA TGG CCA    1049
Glu Tyr Trp Lys Ser Ile Ser Pro Gln Glu Gln His Asp Thr Trp Pro
            240             245             250
GTA CCA ACC TAT CAT GTT GGG GGA TGG TAC GAT ATT TTA CTA AAC GGA    1097
Val Pro Thr Tyr His Val Gly Gly Trp Tyr Asp Ile Leu Leu Asn Gly
            255             260             265
ACA TCT AAA AAC TAT ATT GGG ATT ACA GAA AAT GGT CCG ACA GAA AGA    1145
Thr Ser Lys Asn Tyr Ile Gly Ile Thr Glu Asn Gly Pro Thr Glu Arg
270             275             280             285
TAT TTG CCT GCT TTA GAG AAA ACC GTA AAC ATT CAA GAC ACG CAA AAA    1193
Tyr Leu Pro Ala Leu Glu Lys Thr Val Asn Ile Gln Asp Thr Gln Lys
            290             295             300
TTA TTA ATT GGA CCA TGG ACT CAC GGA TAT CCG CAA ACA GCG GTG GGG    1241
Leu Leu Ile Gly Pro Trp Thr His Gly Tyr Pro Gln Thr Ala Val Gly
            305             310             315
ACG TTT AAT TTT CCA AAA GCT GAT TTG AGC GAT GTG CAC AAT GCT GGC    1289
Thr Phe Asn Phe Pro Lys Ala Asp Leu Ser Asp Val His Asn Ala Gly
            320             325             330
```

*FIG. 4-2*

```
AAT GGG GCA GAT AAT TGG CGG CTT GAG CAA TTA CGC TGG TTT GAT TAC    1337
Asn Gly Ala Asp Asn Trp Arg Leu Glu Gln Leu Arg Trp Phe Asp Tyr
        335             340             345
TGG CTA AAA GGA ATA GAT AAC GGA ATT ATG GAT GAA GAT CCG GTC AAG    1385
Trp Leu Lys Gly Ile Asp Asn Gly Ile Met Asp Glu Asp Pro Val Lys
350             355             360             365
CTT TAT ATT ATG AAG GGT GAA AAT GAT GGC TTC TGG CGC ACG GAA AAG    1433
Leu Tyr Ile Met Lys Gly Glu Asn Asp Gly Phe Trp Arg Thr Glu Lys
            370             375             380
GAG TGG CCG ATA GCT CGC ACC GAA TAT ACA AAC TAC TAT CTT CAT GAT    1481
Glu Trp Pro Ile Ala Arg Thr Glu Tyr Thr Asn Tyr Tyr Leu His Asp
        385             390             395
GGT AAA TCT GGA ACG ATT GAT TCA TTG AAT GAT GGC ATT CTG AGC ACC    1529
Gly Lys Ser Gly Thr Ile Asp Ser Leu Asn Asp Gly Ile Leu Ser Thr
400             405             410
GAA AAG CCA AAA TCT GGT AAA AAA GCT GAT TCT TAT CTT TAT GAT CCG    1577
Glu Lys Pro Lys Ser Gly Lys Lys Ala Asp Ser Tyr Leu Tyr Asp Pro
            415             420             425
AAA AAC CCA ACG CCG ACT GTG GGC GGA AAT ATT AGC GGA ACG ACA CCA    1625
Lys Asn Pro Thr Pro Thr Val Gly Gly Asn Ile Ser Gly Thr Thr Pro
430             435             440             445
AAT GAT GAG CGA GGT CCA CAA GAT CAG CAG GGT ATT GAA AAA GAT GTG    1673
Asn Asp Glu Arg Gly Pro Gln Asp Gln Gln Gly Ile Glu Lys Asp Val
            450             455             460
CTT ACC TAC ACA ACA GAG GTG CTG AAT GAG GAC ACA GAA GTA ACT GGC    1721
Leu Thr Tyr Thr Thr Glu Val Leu Asn Glu Asp Thr Glu Val Thr Gly
        465             470             475
CCG ATT AAG GTG AAG CTT TGG GCA TCA ACT AAC GCT AAG GAC ACT GAC    1769
Pro Ile Lys Val Lys Leu Trp Ala Ser Thr Asn Ala Lys Asp Thr Asp
480             485             490
TTT GCT GTT AAA TTA ACG GAT GTC TAT CCT GAC GGA CGT TCC ATC ATC    1817
Phe Ala Val Lys Leu Thr Asp Val Tyr Pro Asp Gly Arg Ser Ile Ile
            495             500             505
ATT CAA GAC AGC ATT ATC CGC GGC CGA TAC CAT GAA TCC CGT GAA AAA    1865
Ile Gln Asp Ser Ile Ile Arg Gly Arg Tyr His Glu Ser Arg Glu Lys
510             515             520             525
```

*FIG. 4-3*

```
GAA ACC TTA TTA GAG CCA GGG AAA ATC TAT GAA TTT ACG ATT GAC CTA        1913
Glu Thr Leu Leu Glu Pro Gly Lys Ile Tyr Glu Phe Thr Ile Asp Leu
            530                 535                 540
GGC TCA ACG GCT AAT ATA TTT AAA AAG GGA CAT CGC ATC CGT GTA GAT        1961
Gly Ser Thr Ala Asn Ile Phe Lys Lys Gly His Arg Ile Arg Val Asp
            545                 550                 555
GTT TCC AGC AGT AAC TAT CCT AGA TTC GAT AAT AAC CCG AAT ACA GGA        2009
Val Ser Ser Ser Asn Tyr Pro Arg Phe Asp Asn Asn Pro Asn Thr Gly
            560                 565                 570
CAT AAG TTT GGC AAT GAT GCC GCT ATG AAG ACA GCG AAA AAT ACG ATT        2057
His Lys Phe Gly Asn Asp Ala Ala Met Lys Thr Ala Lys Asn Thr Ile
       575                 580                 585
TAT CAT GAT TCA GAG CAT CCG TCA CAT ATT ATA TTG CCA ATT ATT CCA        2105
Tyr His Asp Ser Glu His Pro Ser His Ile Ile Leu Pro Ile Ile Pro
590                 595                 600                 605

TTTGCAAAAT AGGGAAAATT GCTCAATAAT AGAATTGTAC ATAAAGGGGG AATCAGCAAT      2221
GAGAGGAATT ATTCACAACG CAGCACGTGA AATGTCAAAG GAAGATGTGG AAACATTTTT      2281
ACAACAAGCC GAAGTGGTCC ATGTGGCTAC AACCGGAAAA GACGGCTACC CATATGTCAT      2341
TCCTTTGGTG TATGTCTATG AAGGCGGTCC TAAGTTTTAT ATTCATACAG GCAATCTGAG      2401
AGAAAGCCAT TTTGAACAGA ATATTAAAGA AAATCCTCGA GTGTGTATTG AGGTAGAGCA      2461
AATGGGT                                                                2468
```

*FIG. 4-4*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
       ( A ) LENGTH: 9 amino acids
       ( B ) TYPE: amino acid
       ( D ) TOPOLOGY: linear ( i i ) MOLECULE TYPE: peptide ( v ) FRAGMENT TYPE: N-terminal ( x i ) SEQUENCE DESCRIPTION: SEQ ID NO:1:

Gln  Ser  Glu  Gln  Glu  Lys  Ala  Glu  Glu
   1                 5

( 2 ) INFORMATION FOR SEQ ID NO:2:

( i ) SEQUENCE CHARACTERISTICS:
       ( A ) LENGTH: 2468 base pairs
       ( B ) TYPE: nucleic acid
       ( C ) STRANDEDNESS: unknown
       ( D ) TOPOLOGY: unknown ( i i ) MOLECULE TYPE: DNA (genomic)

( i x ) FEATURE:
       ( A ) NAME/KEY: CDS
       ( B ) LOCATION: 210..2111

( i x ) FEATURE:
       ( A ) NAME/KEY: matpeptide
       ( B ) LOCATION: 291..2111

( x i ) SEQUENCE DESCRIPTION: SEQ ID NO:2:

```
TCACATTGAC  AGTTAAGCAA  TTTTTATTAA  ATATTACATA  CCAACTTCCA  CATATATCAA         60

TAAGGTTTAT  ACTTTATTGA  TATAGCAACT  ATAATAATCC  AACTAAATAC  CTATATCCTT        120

TTTCCCGCGA  ATGTCCTATT  TACTTATTTT  TCCTATCGAT  ATAATATTAG  TTTGAAAATT        180

TTAAAAATAA  AGAAAATGGA  GGTGTGTGC   ATG  AAT  AGA  AAG  AAA  AAA  TTT  CTT    233
                                    Met  Asn  Arg  Lys  Lys  Lys  Phe  Leu
                                    -27       -25                      -20

TCT  ATG  CTG  CTG  ACT  GTT  CTT  TTA  GTC  ACA  TCA  TTA  TTT  AGC  AGT  GTG   281
Ser  Met  Leu  Leu  Thr  Val  Leu  Leu  Val  Thr  Ser  Leu  Phe  Ser  Ser  Val
              -15                      -10                        -5

GCT  TTT  GGG  CAG  TCA  GAG  CAG  GAA  AAG  GCA  GAA  GAA  CTT  TAT  CAG  TAT   329
Ala  Phe  Gly  Gln  Ser  Glu  Gln  Glu  Lys  Ala  Glu  Glu  Leu  Tyr  Gln  Tyr
                    1                   5                        10

GAA  CTT  AAG  ACT  GAC  GTT  ATG  GTA  GAA  ATG  CGC  GAT  GGT  GTA  AAA  CTG   377
Glu  Leu  Lys  Thr  Asp  Val  Met  Val  Glu  Met  Arg  Asp  Gly  Val  Lys  Leu
         15                   20                  25
```

| | | | | | | | | | | | | | | | | |
|---|---|---|---|---|---|---|---|---|---|---|---|---|---|---|---|---|
| CCT | ACA | GAT | ATT | TAC | CTG | CCG | GTT | GCC | AAA | ACG | GAG | CAA | GAA | AAG | AAA | 425 |
| Pro | Thr | Asp | Ile | Tyr | Leu | Pro | Val | Ala | Lys | Thr | Glu | Gln | Glu | Lys | Lys | |
| 30 | | | | 35 | | | | | 40 | | | | | 45 | | |
| GAT | GGT | TTT | CCT | ACG | CTT | GTG | TTT | CGA | ACT | CCT | TAC | AAC | AAG | GAT | ACA | 473 |
| Asp | Gly | Phe | Pro | Thr | Leu | Val | Phe | Arg | Thr | Pro | Tyr | Asn | Lys | Asp | Thr | |
| | | | 50 | | | | | 55 | | | | | 60 | | | |
| TAT | GGG | AAA | ACT | GAA | GGT | CCT | TTC | TTT | GCA | AAA | AGA | GGC | TAT | GCA | GTG | 521 |
| Tyr | Gly | Lys | Thr | Glu | Gly | Pro | Phe | Phe | Ala | Lys | Arg | Gly | Tyr | Ala | Val | |
| | | | 65 | | | | | 70 | | | | | 75 | | | |
| GTT | GTT | CAG | GAT | ACA | CGT | GGC | CGC | TAC | AAG | TCA | GAA | GGA | GAA | TGG | AAC | 569 |
| Val | Val | Gln | Asp | Thr | Arg | Gly | Arg | Tyr | Lys | Ser | Glu | Gly | Glu | Trp | Asn | |
| | | 80 | | | | 85 | | | | | 90 | | | | | |
| TTT | GTA | TTT | GAT | GAT | GCC | AAG | GAT | GGC | TAT | GAT | TTA | ATT | GAA | TGG | GCT | 617 |
| Phe | Val | Phe | Asp | Asp | Ala | Lys | Asp | Gly | Tyr | Asp | Leu | Ile | Glu | Trp | Ala | |
| | 95 | | | | 100 | | | | | 105 | | | | | | |
| GCA | GTT | CAG | GAT | TTC | AGT | ACT | GGG | AAG | GTT | GGC | ACA | ATG | GGC | CTA | TCT | 665 |
| Ala | Val | Gln | Asp | Phe | Ser | Thr | Gly | Lys | Val | Gly | Thr | Met | Gly | Leu | Ser | |
| 110 | | | | 115 | | | | | 120 | | | | | 125 | | |
| TAC | ATG | GCC | TAT | ACC | CAG | TAT | GTA | TTG | GCT | GAA | TCA | AAA | CCG | CCT | CAT | 713 |
| Tyr | Met | Ala | Tyr | Thr | Gln | Tyr | Val | Leu | Ala | Glu | Ser | Lys | Pro | Pro | His | |
| | | | 130 | | | | | 135 | | | | | 140 | | | |
| CTT | GTT | ACA | ATG | ATT | CCG | CTT | GAA | GGG | ATG | AGC | AAT | CCT | GCT | GAA | GAA | 761 |
| Leu | Val | Thr | Met | Ile | Pro | Leu | Glu | Gly | Met | Ser | Asn | Pro | Ala | Glu | Glu | |
| | | | 145 | | | | | 150 | | | | | 155 | | | |
| GTC | TTT | TTT | ACA | GGC | GGA | GCT | ATG | CAG | CTA | GAC | CGC | TAT | TTA | TCA | TGG | 809 |
| Val | Phe | Phe | Thr | Gly | Gly | Ala | Met | Gln | Leu | Asp | Arg | Tyr | Leu | Ser | Trp | |
| | | 160 | | | | | 165 | | | | | 170 | | | | |
| ACT | TTG | GGC | CAG | GCG | GTA | GAT | ACA | GCA | AGA | CGA | CTT | GAC | GAA | AAG | AAT | 857 |
| Thr | Leu | Gly | Gln | Ala | Val | Asp | Thr | Ala | Arg | Arg | Leu | Asp | Glu | Lys | Asn | |
| | 175 | | | | | 180 | | | | | 185 | | | | | |
| GGA | AAT | ACT | GTT | AAC | CAG | GAT | AAG | ATT | AAA | AAA | GCG | TTA | GAT | GAT | TAT | 905 |
| Gly | Asn | Thr | Val | Asn | Gln | Asp | Lys | Ile | Lys | Lys | Ala | Leu | Asp | Asp | Tyr | |
| 190 | | | | | 195 | | | | | 200 | | | | | 205 | |
| GAG | AAG | TGG | CTT | AAT | CAT | ATG | CCA | AGA | TCT | AAG | GTG | GCA | CCA | TTA | AAC | 953 |
| Glu | Lys | Trp | Leu | Asn | His | Met | Pro | Arg | Ser | Lys | Val | Ala | Pro | Leu | Asn | |
| | | | | 210 | | | | | 215 | | | | | 220 | | |
| CAA | ATG | ATT | GAT | TGG | TGG | AAA | GAA | GCG | ATG | GAT | CAT | CCT | GAG | TAT | GAC | 1001 |
| Gln | Met | Ile | Asp | Trp | Trp | Lys | Glu | Ala | Met | Asp | His | Pro | Glu | Tyr | Asp | |
| | | | 225 | | | | | 230 | | | | | 235 | | | |
| GAG | TAT | TGG | AAG | AGC | ATC | TCT | CCT | CAG | GAA | CAA | CAT | GAT | ACA | TGG | CCA | 1049 |
| Glu | Tyr | Trp | Lys | Ser | Ile | Ser | Pro | Gln | Glu | Gln | His | Asp | Thr | Trp | Pro | |
| | | 240 | | | | | 245 | | | | | 250 | | | | |
| GTA | CCA | ACC | TAT | CAT | GTT | GGG | GGA | TGG | TAC | GAT | ATT | TTA | CTA | AAC | GGA | 1097 |
| Val | Pro | Thr | Tyr | His | Val | Gly | Gly | Trp | Tyr | Asp | Ile | Leu | Leu | Asn | Gly | |
| | 255 | | | | | 260 | | | | | 265 | | | | | |
| ACA | TCT | AAA | AAC | TAT | ATT | GGG | ATT | ACA | GAA | AAT | GGT | CCG | ACA | GAA | AGA | 1145 |
| Thr | Ser | Lys | Asn | Tyr | Ile | Gly | Ile | Thr | Glu | Asn | Gly | Pro | Thr | Glu | Arg | |
| 270 | | | | | 275 | | | | | 280 | | | | | 285 | |
| TAT | TTG | CCT | GCT | TTA | GAG | AAA | ACC | GTA | AAC | ATT | CAA | GAC | ACG | CAA | AAA | 1193 |
| Tyr | Leu | Pro | Ala | Leu | Glu | Lys | Thr | Val | Asn | Ile | Gln | Asp | Thr | Gln | Lys | |
| | | | | 290 | | | | | 295 | | | | | 300 | | |
| TTA | TTA | ATT | GGA | CCA | TGG | ACT | CAC | GGA | TAT | CCG | CAA | ACA | GCG | GTG | GGG | 1241 |
| Leu | Leu | Ile | Gly | Pro | Trp | Thr | His | Gly | Tyr | Pro | Gln | Thr | Ala | Val | Gly | |
| | | | 305 | | | | | 310 | | | | | 315 | | | |
| ACG | TTT | AAT | TTT | CCA | AAA | GCT | GAT | TTG | AGC | GAT | GTG | CAC | AAT | GCT | GGC | 1289 |
| Thr | Phe | Asn | Phe | Pro | Lys | Ala | Asp | Leu | Ser | Asp | Val | His | Asn | Ala | Gly | |
| | | 320 | | | | | 325 | | | | | 330 | | | | |
| AAT | GGG | GCA | GAT | AAT | TGG | CGG | CTT | GAG | CAA | TTA | CGC | TGG | TTT | GAT | TAC | 1337 |
| Asn | Gly | Ala | Asp | Asn | Trp | Arg | Leu | Glu | Gln | Leu | Arg | Trp | Phe | Asp | Tyr | |
| | 335 | | | | | 340 | | | | | 345 | | | | | |
| TGG | CTA | AAA | GGA | ATA | GAT | AAC | GGA | ATT | ATG | GAT | GAA | GAT | CCG | GTC | AAG | 1385 |

```
Trp Leu Lys Gly Ile Asp Asn Gly Ile Met Asp Glu Asp Pro Val Lys
350                 355                 360                 365

CTT TAT ATT ATG AAG GGT GAA AAT GAT GGC TTC TGG CGC ACG GAA AAG             1433
Leu Tyr Ile Met Lys Gly Glu Asn Asp Gly Phe Trp Arg Thr Glu Lys
                370                 375                 380

GAG TGG CCG ATA GCT CGC ACC GAA TAT ACA AAC TAC TAT CTT CAT GAT             1481
Glu Trp Pro Ile Ala Arg Thr Glu Tyr Thr Asn Tyr Tyr Leu His Asp
            385                 390                 395

GGT AAA TCT GGA ACG ATT GAT TCA TTG AAT GAT GGC ATT CTG AGC ACC             1529
Gly Lys Ser Gly Thr Ile Asp Ser Leu Asn Asp Gly Ile Leu Ser Thr
            400                 405                 410

GAA AAG CCA AAA TCT GGT AAA AAA GCT GAT TCT TAT CTT TAT GAT CCG             1577
Glu Lys Pro Lys Ser Gly Lys Lys Ala Asp Ser Tyr Leu Tyr Asp Pro
        415                 420                 425

AAA AAC CCA ACG CCG ACT GTG GGC GGA AAT ATT AGC GGA ACG ACA CCA             1625
Lys Asn Pro Thr Pro Thr Val Gly Gly Asn Ile Ser Gly Thr Thr Pro
430                 435                 440                 445

AAT GAT GAG CGA GGT CCA CAA GAT CAG CAG GGT ATT GAA AAA GAT GTG             1673
Asn Asp Glu Arg Gly Pro Gln Asp Gln Gln Gly Ile Glu Lys Asp Val
                450                 455                 460

CTT ACC TAC ACA ACA GAG GTG CTG AAT GAG GAC ACA GAA GTA ACT GGC             1721
Leu Thr Tyr Thr Thr Glu Val Leu Asn Glu Asp Thr Glu Val Thr Gly
            465                 470                 475

CCG ATT AAG GTG AAG CTT TGG GCA TCA ACT AAC GCT AAG GAC ACT GAC             1769
Pro Ile Lys Val Lys Leu Trp Ala Ser Thr Asn Ala Lys Asp Thr Asp
            480                 485                 490

TTT GCT GTT AAA TTA ACG GAT GTC TAT CCT GAC GGA CGT TCC ATC ATC             1817
Phe Ala Val Lys Leu Thr Asp Val Tyr Pro Asp Gly Arg Ser Ile Ile
        495                 500                 505

ATT CAA GAC AGC ATT ATC CGC GGC CGA TAC CAT GAA TCC CGT GAA AAA             1865
Ile Gln Asp Ser Ile Ile Arg Gly Arg Tyr His Glu Ser Arg Glu Lys
510                 515                 520                 525

GAA ACC TTA TTA GAG CCA GGG AAA ATC TAT GAA TTT ACG ATT GAC CTA             1913
Glu Thr Leu Leu Glu Pro Gly Lys Ile Tyr Glu Phe Thr Ile Asp Leu
                530                 535                 540

GGC TCA ACG GCT AAT ATA TTT AAA AAG GGA CAT CGC ATC CGT GTA GAT             1961
Gly Ser Thr Ala Asn Ile Phe Lys Lys Gly His Arg Ile Arg Val Asp
            545                 550                 555

GTT TCC AGC AGT AAC TAT CCT AGA TTC GAT AAT AAC CCG AAT ACA GGA             2009
Val Ser Ser Ser Asn Tyr Pro Arg Phe Asp Asn Asn Pro Asn Thr Gly
            560                 565                 570

CAT AAG TTT GGC AAT GAT GCC GCT ATG AAG ACA GCG AAA AAT ACG ATT             2057
His Lys Phe Gly Asn Asp Ala Ala Met Lys Thr Ala Lys Asn Thr Ile
        575                 580                 585

TAT CAT GAT TCA GAG CAT CCG TCA CAT ATT ATA TTG CCA ATT ATT CCA             2105
Tyr His Asp Ser Glu His Pro Ser His Ile Ile Leu Pro Ile Ile Pro
590                 595                 600                 605

AAT GAA TAATTTCAAG GGGCTGGCTC ACGTGCCAGC CCTGTTTTTT TTCAAAAGCT              2161
Asn Glu
TTTGCAAAAT AGGGAAAATT GCTCAATAAT AGAATTGTAC ATAAAGGGGG AATCAGCAAT           2221
GAGAGGAATT ATTCACAACG CAGCACGTGA AATGTCAAAG GAAGATGTGG AAACATTTTT           2281
ACAACAAGCC GAAGTGGTCC ATGTGGCTAC AACCGGAAAA GACGGCTACC CATATGTCAT           2341
TCCTTTGGTG TATGTCTATG AAGGCGGTCC TAAGTTTTAT ATTCATACAG GCAATCTGAG           2401
AGAAAGCCAT TTTGAACAGA ATATTAAAGA AAATCCTCGA GTGTGTATTG AGGTAGAGCA           2461
AATGGGT                                                                    2468
```

( 2 ) INFORMATION FOR SEQ ID NO:3:

( i ) SEQUENCE CHARACTERISTICS:
        ( A ) LENGTH: 634 amino acids

-continued (B) TYPE: amino acid
(D) TOPOLOGY: linear (ii) MOLECULE TYPE: protein (xi) SEQUENCE DESCRIPTION: SEQ ID NO:3:

| Met -27 | Asn | Arg -25 | Lys | Lys | Lys | Phe | Leu -20 | Ser | Met | Leu | Leu | Thr | Leu -15 | Val | Leu |
| Val | Thr -10 | Ser | Leu | Phe | Ser | Ser -5 | Val | Ala | Phe | Gly | Gln | Ser 1 | Glu | Gln | Glu 5 |
| Lys | Ala | Glu | Glu | Leu 10 | Tyr | Gln | Tyr | Glu | Leu 15 | Lys | Thr | Asp | Val | Met 20 | Val |
| Glu | Met | Arg | Asp 25 | Gly | Val | Lys | Leu | Pro 30 | Thr | Asp | Ile | Tyr | Leu 35 | Pro | Val |
| Ala | Lys | Thr 40 | Glu | Gln | Glu | Lys | Lys 45 | Asp | Gly | Phe | Pro | Thr 50 | Leu | Val | Phe |
| Arg | Thr 55 | Pro | Tyr | Asn | Lys | Asp 60 | Thr | Tyr | Gly | Lys | Thr 65 | Glu | Gly | Pro | Phe |
| Phe 70 | Ala | Lys | Arg | Gly | Tyr 75 | Ala | Val | Val | Val | Gln 80 | Asp | Thr | Arg | Gly | Arg 85 |
| Tyr | Lys | Ser | Glu | Gly 90 | Glu | Trp | Asn | Phe | Val 95 | Phe | Asp | Asp | Ala | Lys 100 | Asp |
| Gly | Tyr | Asp | Leu 105 | Ile | Glu | Trp | Ala | Ala 110 | Val | Gln | Asp | Phe | Ser 115 | Thr | Gly |
| Lys | Val | Gly 120 | Thr | Met | Gly | Leu | Ser 125 | Tyr | Met | Ala | Tyr | Thr 130 | Gln | Tyr | Val |
| Leu | Ala 135 | Glu | Ser | Lys | Pro | Pro 140 | His | Leu | Val | Thr | Met 145 | Ile | Pro | Leu | Glu |
| Gly 150 | Met | Ser | Asn | Pro | Ala 155 | Glu | Glu | Val | Phe | Phe 160 | Thr | Gly | Gly | Ala | Met 165 |
| Gln | Leu | Asp | Arg | Tyr 170 | Leu | Ser | Trp | Thr | Leu 175 | Gly | Gln | Ala | Val | Asp 180 | Thr |
| Ala | Arg | Arg | Leu 185 | Asp | Glu | Lys | Asn | Gly 190 | Asn | Thr | Val | Asn | Gln 195 | Asp | Lys |
| Ile | Lys | Lys 200 | Ala | Leu | Asp | Asp | Tyr 205 | Glu | Lys | Trp | Leu | Asn 210 | His | Met | Pro |
| Arg | Ser 215 | Lys | Val | Ala | Pro | Leu 220 | Asn | Gln | Met | Ile | Asp 225 | Trp | Trp | Lys | Glu |
| Ala 230 | Met | Asp | His | Pro | Glu 235 | Tyr | Asp | Glu | Tyr | Trp 240 | Lys | Ser | Ile | Ser | Pro 245 |
| Gln | Glu | Gln | His | Asp 250 | Thr | Trp | Pro | Val | Pro 255 | Thr | Tyr | His | Val | Gly 260 | Gly |
| Trp | Tyr | Asp | Ile 265 | Leu | Leu | Asn | Gly | Thr 270 | Ser | Lys | Asn | Tyr | Ile 275 | Gly | Ile |
| Thr | Glu | Asn 280 | Gly | Pro | Thr | Glu | Arg 285 | Tyr | Leu | Pro | Ala | Leu 290 | Glu | Lys | Thr |
| Val | Asn 295 | Ile | Gln | Asp | Thr | Gln 300 | Lys | Leu | Leu | Ile | Gly 305 | Pro | Trp | Thr | His |
| Gly | Tyr | Pro | Gln 310 | Thr | Ala | Val 315 | Gly | Thr | Phe | Asn 320 | Phe | Pro | Lys | Ala | Asp 325 |
| Leu | Ser | Asp | Val | His 330 | Asn | Ala | Gly | Asn 335 | Gly | Ala | Asp | Asn | Trp 340 | Arg | Leu |
| Glu | Gln | Leu | Arg 345 | Trp | Phe | Asp | Tyr | Trp 350 | Leu | Lys | Gly | Ile | Asp 355 | Asn | Gly |
| Ile | Met | Asp 360 | Glu | Asp | Pro | Val | Lys 365 | Leu | Tyr | Ile | Met | Lys 370 | Gly | Glu | Asn |

```
Asp Gly Phe Trp Arg Thr Glu Lys Glu Trp Pro Ile Ala Arg Thr Glu
    375             380             385

Tyr Thr Asn Tyr Tyr Leu His Asp Gly Lys Ser Gly Thr Ile Asp Ser
390             395             400                         405

Leu Asn Asp Gly Ile Leu Ser Thr Glu Lys Pro Lys Ser Gly Lys Lys
                410             415                     420

Ala Asp Ser Tyr Leu Tyr Asp Pro Lys Asn Pro Thr Pro Thr Val Gly
            425             430                     435

Gly Asn Ile Ser Gly Thr Thr Pro Asn Asp Glu Arg Gly Pro Gln Asp
        440             445                     450

Gln Gln Gly Ile Glu Lys Asp Val Leu Thr Tyr Thr Thr Glu Val Leu
    455             460                     465

Asn Glu Asp Thr Glu Val Thr Gly Pro Ile Lys Val Lys Leu Trp Ala
470             475                 480                     485

Ser Thr Asn Ala Lys Asp Thr Asp Phe Ala Val Lys Leu Thr Asp Val
            490                 495                     500

Tyr Pro Asp Gly Arg Ser Ile Ile Ile Gln Asp Ser Ile Ile Arg Gly
            505             510                     515

Arg Tyr His Glu Ser Arg Glu Lys Glu Thr Leu Leu Glu Pro Gly Lys
        520             525                     530

Ile Tyr Glu Phe Thr Ile Asp Leu Gly Ser Thr Ala Asn Ile Phe Lys
    535             540                 545

Lys Gly His Arg Ile Arg Val Asp Val Ser Ser Ser Asn Tyr Pro Arg
550             555                 560                     565

Phe Asp Asn Asn Pro Asn Thr Gly His Lys Phe Gly Asn Asp Ala Ala
                570             575                     580

Met Lys Thr Ala Lys Asn Thr Ile Tyr His Asp Ser Glu His Pro Ser
            585             590                     595

His Ile Ile Leu Pro Ile Ile Pro Asn Glu
        600             605
```

GL-7ACA ACYLASE

The invention relates to a new GL-7ACA acylase (hereinafter referred to as "GL-7ACA acylase J1"). More particularly, it relates to a new GL-7ACA acylase derived from *Bacillus laterosporus* J1, a DNA encoding thereof, an expression vector containing said DNA, a microorganism transformed with said expression vector, and the production of the GL-7ACA acylase by culturing said transformant.

GL-7ACA acylase is a general term for an enzyme, which is, in common, capable of hydrolyzing 7-(4-carboxybutanamido)-3-acetoxymethyl-3-cephem-4-carboxylic acid (GL-7ACA) to 7-aminocephalosporan (7-ACA). 7-ACA has been made by methods of chemical conversion of cephalosporin C such as iminoether or nitrosyl chloride method. However, to make cost reduction, an alternative method utilizing enzymatic conversion has been searched for a long time since similar enzymatic conversion was successfully adopted for the production of 6-aminopenicillanic acid (6-APA) which is a starting material for penicillins, another family of β-lactam antibiotics. In the course of such efforts, two step enzymatic conversion was devised using D-amino acid oxidase and GL-7ACA acylase. This method has been industrialized as the one where the enzymatic oxidation was substituted by chemical oxidation.

It was reported that Pseudomonas sp. GK16 produced a GL-7ACA acylase and a part of nucleotide sequence of the said acylase gene was clarified [Cf. J., Bacteriol., 163, 1222–1228 (1985)].

The inventors of this invention have conducted extensive studies for searching new GL-7ACA acylases, and as the results, the present inventors have been found a new characteristic GL-7ACA acylase J1 in the cultured broth of a newly isolated organism, *Bacillus laterosporus* J1 and established industrial production of this enzyme. The GL-7ACA acylase J1 of this invention, as compared with the prior GL-7ACA acylases, is characterized by higher thermostability, its entirely different structure from that of the prior acylase and so on, and further characteristics of this GL-7ACA acylase will be apparent from the description mentioned below.

A strain named *Bacillus laterosporus* J1 which is a GL-7ACA acylase producer was newly isolated from a soil sample collected in Iwate Prefecture, Japan.

*Bacillus laterosporus* J1 has the following morphological and physiological characteristics and identified as *Bacillus laterosporus* according to Bergey's Manual of Systematic Bacteriology (Volume 1). The method described in Bergey's Manual was employed principally for this taxonomic study.

1. Morphological characteristics.

Morphological observation of the strain J1 was carried out by the optical microscope with cells grown in Trypticase soy broth (BBL Co., Ltd., U.S.A.) at 37° C.

Strain J1 was a gram-positive, motile bacterium. The cell shapes were rod. Results are shown in Table 1.

TABLE 1

| Morphological characteristics of strain J1. | |
|---|---|
| gram stain | positive |
| color of colony | cream |
| cell shape | rod |
| spore | positive |
| motility | positive |

2. Physiological characteristics

Physiological characteristics of the strain J1 were summarized in Table 2.

The strain J1 was oxidase positive, catalase positive and 0-F test negative. Gelatin was not liquefied and esculin hydrolysis was negative. Nitrate was reduced with production of $N_2$ gas. Ribose, sucrose, trehalose and xylose were fermented. Lysine and ornithine were not decarboxylized and arginine was not hydrolyzed. Indole test was negative. Voges-Proskauer test was negative.

TABLE 2

| Physiological characteristics of the strain J1. | |
|---|---|
| Conditions | Characteristics |
| growth | |
| in air | + |
| in anaerobe | − |
| at pH 6.8 | + |
| at pH 5.8 | − |
| at 2% NaCl | + |
| at 5% NaCl | − |
| at 10° C. | − |
| at 23° C. | + |
| at 30° C. | + |
| at 37° C. | + |
| at 45° C. | + |
| pigment | − |
| catalase | + |
| oxidase | + |
| OF-test | − |
| TSI | −/− |
| IPA | − |
| $H_2S$ (SIM medium) | − |
| $H_2S$ (lead acetate) | − |
| indole | − |
| VP | − |
| Simmons citrate | − |
| urease (Christensen) | +w |
| gelatin liquefaction | − |
| esculin hydrolysis | − |
| nitrate reduction/gas | +/+ |
| lysine decarboxylase | − |
| ornithine decarboxylase | − |
| arginine dihydrolase | − |
| acylamidase | − |
| utilization of | |
| adonitol | − |
| arabinose | − |
| cellobiose | − |
| dulcitol | − |
| fructose | − |
| glucose | − |
| galactose | − |
| glycerol | − |
| inositol | − |
| inulin | − |
| lactose | − |
| maltose | − |
| mannitol | − |
| meribiose | − |
| raffinose | − |
| rhamnose | − |
| ribose | + |
| salicin | − |
| starch | − |
| sucrose | + |
| trehalose | + |
| xylose | + |
| mole % G + C | 40.0 |

The new GL-7ACA acylase of this invention has the following characteristics.

Namely, the new GL-7ACA acylase of this invention
(a) has ability to catalyze the enzymatic conversion of glutaryl 7-ACA, adipyl 7-ACA, and succinyl 7-ACA, into 7-aminocephalosporanic acid,
(b) has a molecular weight of 70,000 dalton (SDS-PAGE) and
(c) has N-terminal amino acid sequence (SEQ ID NO: 1) of the enzyme: Gln-Ser-Glu-Gln-Glu-Lys-Ala-Glu-Glu.

The new GL-7ACA acylase of this invention can be prepared by recombinant DNA technology, polypeptide synthesis and the like.

Namely, the new GL-7ACA acylase can be prepared by culturing a host cell transformed with an expression vector comprising DNA encoding amino acid sequence of the new GL-7ACA acylase in a nutrient medium and recovering the new GL-7ACA acylase from the cultured broth.

In this process, particulars of which are explained in more detail as follows.

The host cell may include microorganisms [bacteria (e.g. *Escherichia coli, Bacillus subtilis*, etc.), yeast (e.g. *Saccharomyces cerevisiae*. etc.), animal cell lines and cultured plant cells]. Preferred examples of the microorganism may include bacteria, especially a strain belonging to the genus *Escherichia* (e.g. E. coli JM109 ATCC 53323, *E. coli* HB101 ATCC 33694, *E. coli* HB101-16 FERM BP-1872, *E. coli* 294 ATCC 31446, etc.), or the genus *Bacillus* (e.g. *Bacillus subtilis* ISW1214, etc.), yeast, especially a strain belonging to the genus *Saccharomyces* [e.g. *Saccharomyces cerevisiae* AH22], animal cell lines [e.g. mouse L929 cell, Chinese hamster ovary (CHO) cell etc.] and the like.

When bacterium, especially *E. coli* and *Bacillus subtilis* is used as a host cell, the expression vector is usually composed of at least promoter, initiation codon, DNA encoding amino acid sequence of the new GL-7ACA acylase, termination codon, terminator region and replicatable unit. When yeasts or animal cells are used as host cells, the expression vector is preferably composed of at least promoter, initiation codon, DNA encoding amino acid sequences of the signal peptide and the new GL-7ACA acylase and termination codon, and it is possible that enhancer sequence, 5'- and 3'-noncoding region of the new GL-7ACA acylase, splicing junctions, polyadenylation site and replicatable unit are also inserted into the expression vector.

The promoter for expression of the new GL-7ACA acylase in bacteria comprises promoter and Shine-Dalgarno (SD) sequence (e.g. AAGG, etc.). Preferable promoter for bacterial expression may include conventionally employed promoter (e.g. PL-promoter and trp-promoter for *E. coli*) and promoter of the GL-7ACA acylase J1 chromosomal gene. The promoter for expression of the new GL-7ACA acylase in yeast may include the promoter of the TRP1 gene, the ADHI or ADHII gene and acid phosphatase (PH05) gene for *S. cerevisiae* and the promoter for expression of the new GL-7ACA acylase in mammalian cells may include SV40 early or late-promoter, HTLV-LTR-promoter, mouse metallothionein I(MMT)-promoter, vaccinia-promoter and the like.

Preferable initiation codon may include methionine codon (ATG).

The signal peptide may include a signal peptide of conventionally employed other enzymes (e.g. signal peptide of the native t-PA, signal peptide of the native plasminogen) and the like.

The DNA encoding amino acid sequence of the signal peptide or the new GL-7ACA acylase can be prepared in a conventional manner such as a partial or whole DNA synthesis using DNA synthesizer and/or treatment of the complete DNA sequence coding for the new GL-7ACA acylase inserted in a suitable vector [e.g. pACYJ1-3]obtainable from a transformant [e.g. *E. coli* JM109 (pACYJ1-3) FERM BP-3105]with a suitable enzyme (e.g. restriction enzyme, alkaline phosphatase, polynucleotide kinase, DNA ligase, DNA polymerase, etc.).

The termination codon(s) may include a conventionally employed termination codon (e.g. TAG, TGA, etc.).

The terminator region may include natural or synthetic terminator (e.g. terminator of the GL-7ACA J1 chromosomal gene, synthetic fd phage terminator, etc.).

The replicatable unit is a DNA compound having capable of replicating the whole DNA sequence belonging thereto in a host cell and may include natural plasmid, artificially modified plasmid (e.g. DNA fragment prepared from natural plasmid) and synthetic plasmid and preferable examples of the plasmid may include plasmid pBR322 or artificially modified thereof (DNA fragment obtained from a suitable restriction enzyme treatment of pBR322) for *E. coli*, yeast 2 μ plasmid or yeast chromosomal DNA for yeast, plasmid pRSVneo ATCC 37198, plasmid pSV2dhfr ATCC 37145, plasmid pdBPV-MMTneo ATCC 37224, plasmid pSV2neo ATCC 37149 for mammalian cells.

The enhancer sequence may include the enhancer sequence (72 b.p.) of SV40.

The polyadenylation site may include the polyadenylation site of SV40.

The splicing junction may include the splicing junction of SV40.

The promoter, initiation codon, DNA encoding amino acid sequence of the new GL-7ACA acylase, termination codon(s) and terminator region can consecutively and circularly be linked with an adequate replicatable unit (plasmid) together, if desired, using an adequate DNA fragment(s) (e.g. linker, other restriction site, etc.) in a conventional manner (e.g. digestion with restriction enzyme, ligation using T4 DNA ligase) to give an expression vector. When mammalian cells are used as host cells, it is possible that enhancer sequence, promoter, 5'-noncoding region of the cDNA of the new GL-7ACA acylase, initiation codon, DNA encoding amino acid sequences of the signal peptide and the new GL-7ACA acylase, termination codon(s), 3'-noncoding region of the cDNA of the new GL-7ACA acylase, splicing junctions and polyadenylation site are consecutively and circularly linked with an adequate replicatable unit together in the above manner.

A host cell can be transformed (transfected) with the expression vector. Transformation (transfection) can be carried out in a conventional manner [e.g. Kushner method for *E. coli*, calcium phosphate method for mammalian cells, microinjection, etc.] to give a transformant (transfectant).

For the production of the new GL-7ACA acylase in the process of this invention, thus obtained transformant comprising the expression vector is cultured in an aqueous nutrient medium.

The nutrient medium may contain carbon source(s) (e.g. glucose, glycerine, mannitol, fructose, lactose, etc.) and inorganic or organic nitrogen source(s) (e.g. ammonium sulfate, ammonium chloride, hydrolysate of casein, yeast extract, polypeptone, bactotrypton, beef extract, etc.). If desired, other nutritious sources [e.g. inorganic salts (e.g. sodium or potassium biphosphate, dipotassium hydrogen phosphate, magnesium chloride, magnesium sulfate, calcium chloride), vitamins (e.g. vitamin $B_1$), antibiotics (e.g. ampicillin, kanamycin), etc.] may be added to the medium. For the culture of mammalian cells, Dulbecco's Modified Eagle's Minimum Essential Medium (DMEM) supplemented with fetal calf serum and an antibiotic is often used.

The culture of the transformant (including transfectant) may usually be carried out at pH 5.5–8.5 (preferably pH 7–7.5) and 18°–40° C. (preferably 25°–38° C.) for 5–50 hours.

When thus produced new GL-7ACA acylase exists in the culture solution, culture filtrate (supernatant) is obtained by filtration or centrifugation of the cultured broth. From the culture filtrate, the new GL-7ACA acylase can be purified in a conventional manner as generally employed for the purification and isolation of natural or synthetic proteins (e.g. dialysis, gel filtration, affinity column chromatography using anti-GL-7ACA acylase monoclonal antibody, column chromatography on a suitable adsorbent, high performance liquid chromatography, etc.). When the produced new GL-7ACA acylase exists in periplasm and cytoplasm of the cultured transformant, the cells are collected by filtration and centrifugation, and the cell wall and/or cell membrane thereof are destroyed by, for example, treatment with super sonic waves and/or lysozyme to give debris. The debris can be dissolved in a suitable aqueous solution (e.g. 8M aqueous urea, 6M aqueous guanidium salts). From the solution, the new GL-7ACA acylase can be purified in a conventional manner as exemplified above. If it is necessary to refold the new GL-7ACA acylase produced in E. coli, the refolding can be carried out in a conventional manner.

This invention further provides a process for the preparation of a compound of the formula:

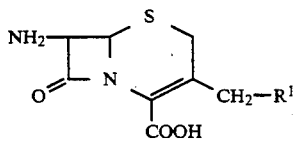

wherein $R^1$ is acetoxy, hydroxy and hydrogen or its salt, which comprises contacting a compound of the formula:

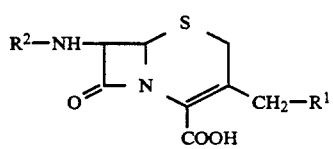

wherein
$R^1$ is the same as defined above and
$R^2$ is carboxy($C_1$–$C_6$)alkanoyl or D-glutamyl or its salt, with the cultured broth of a microorganism transformed with an expression vector comprising DNA encoding the new GL-7ACA acylase of this invention or its processed material.

The carboxy($C_1$–$C_6$)alkanoyl for $R^2$ may include glutaryl, succinyl, adipyl and the like.

Suitable salt of the compounds (I) and (II) may be alkali metal salt (e.g. sodium salt, potassium salt).

If the GL-7ACA acylase activity exists in transformed cells, the following preparations can be exemplified as a processed material of the cultured broth.

(1) Raw cells; separated from the cultured broth in a conventional manner such as filtration and centrifugation, (2) dried cells; obtained by drying said raw cells in a conventional manner such as lyophilization and vacuum drying, (3) cell-free extract; obtained by destroying said raw or dried cells in a conventional manner (e.g. autolysis of the cells using an organic solvent, grinding the cells with alumina, sea sand, etc. or treating the cells with super sonic waves), (4) enzyme solution; obtained by purification or partial purification of said cell-free extracts in a conventional manner (e.g. column chromatography) and (5) immobilized cells or enzyme; prepared by immobilizing said cells or enzyme in a conventional manner (e.g. a method using acrylamide, glass bead, ion exchange resin, etc.).

If the GL-7ACA acylase activity exists in a culture filtrate of transformed cells, the culture filtrate (supernatant), enzyme solution and immobilized cells or enzymes can be exemplified as a processed material of the cultured broth.

The reaction comprising a contact of the compound (II) with the enzyme can be conducted in an aqueous medium such as water or a buffer solution, that is, it can be usually conducted by dissolving or suspending the cultured broth or its processed material in an aqueous medium such as water or a buffer solution containing the compound (II).

Preferable pH of the reaction mixture, concentration of the compound (II), reaction time and reaction temperature may vary with properties of a cultured broth or its processed material to be used. Generally, the reaction is carried out at pH 6 to 9, preferably pH 7 to 9, at 5° to 50° C., preferably 20° to 45° C. for 2 to 50 hours.

The concentration of the compound (II) as a substrate in the reaction mixture may be preferably selected from a range of 1 to 100 mg/ml.

Thus produced compound (I) can be purified and isolated from the reaction mixture in a conventional manner.

Brief explanation of the accompanying drawings is as follows.

FIGS. 4-1 through 4-4 show nucleotide sequence (SEQ ID NO. 2) and deduced amino acid sequence (SEQ ID NO: 3) of the GL-7ACA acylase J1 chromosomal gene.

Figure 1:
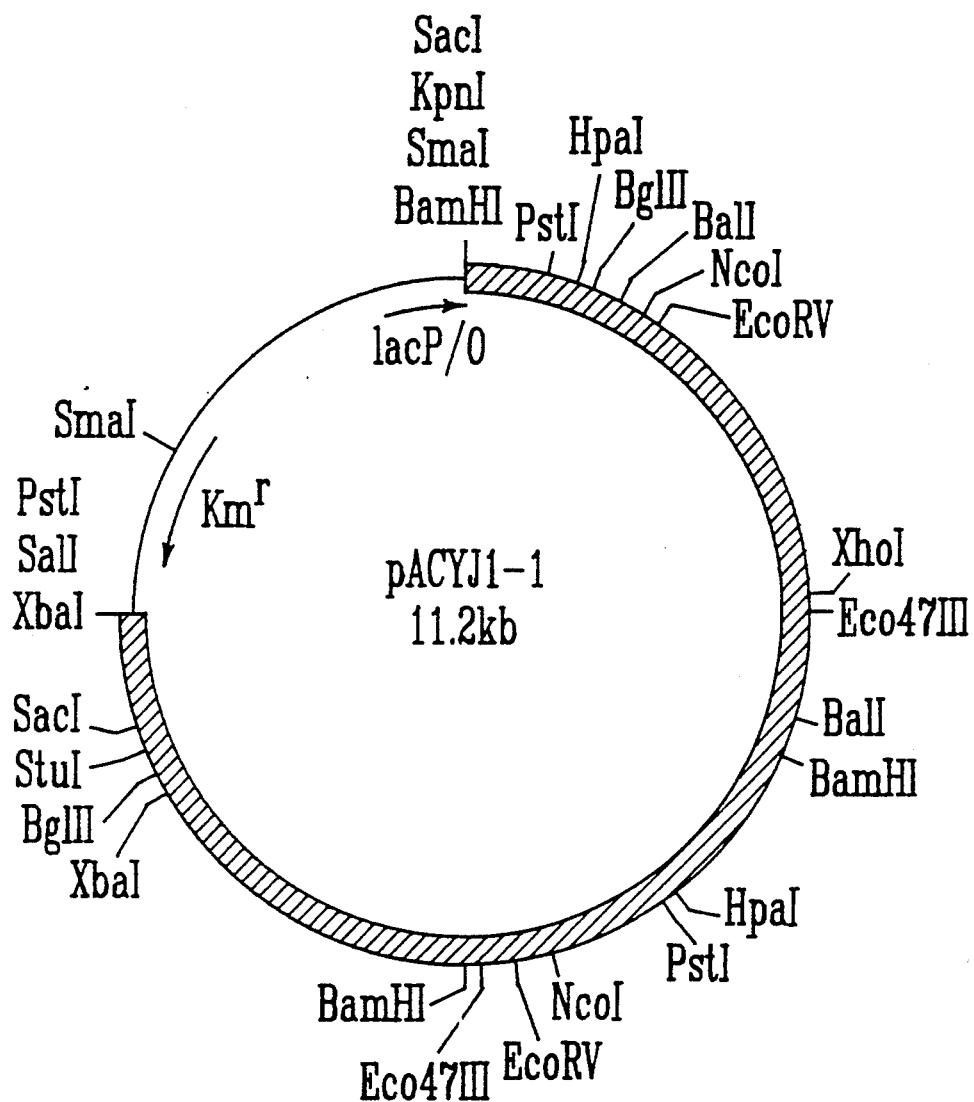
FIG. 1 shows restriction cleavage map of plasmid pACYJ1-1.

In the following Examples, some plasmids, enzymes, such as restriction enzymes, T4 DNA ligases, and other materials were obtained from commercial sources and used according to the indication by suppliers. Operations employed for the cloning of DNA, transformation of host cells, cultivation of transformants, recovery of the new GL-7ACA acylase from the cultured broth, and the like are well known in the art or can be adapted from literatures.

Following Examples are given for the purpose of illustrating this invention, but not limited thereto.

EXAMPLE 1

Isolation of the gene encoding GL-7ACA acylase of *Bacillus laterosporus J1*

1.1. Preparation of chromosomal DNA of *B. laterosporus* J1.

Chromosomal DNA of *Bacillus laterosporus* J1 was prepared according to the method of Harris-Warrick et al., Proc. Natl. Acad. Sci., USA 72: 2207-2211, 1975. *B. laterosporus* J1 was grown at 30° C. for 40 hours on Bouillon agar (Eiken Chemical Co., Ltd.), suspended in saline, harvested by centrifugation and washed once with 50 mM Tris-HCl (pH 8) containing 1 mM EDTA. Resultant cell pellets of approximately 9 g (wet weight) was suspended in 20 ml of 50 mM Tris-HCl (pH 8) containing 20% sucrose and 1 mM EDTA and treated with 25 mg of lysozyme at 37° C. for 30 min. Furthermore, to this suspension, 50 ml of 100 mM EDTA (pH 9.6)-1% lauroyl sarcosylate and 10 ml of 5 mg/ml of pronase E were added and the resultant mixture was incubated at 50° C. for 2 hours. After addition of 1.25 g of CsCl to each 1 ml of the lysate, it was applied to equilibrium density gradient centrifugation. After centrifugation, chromosomal DNA fractions were pooled and dialyzed against 10 mM Tris-HCl (pH 8) containing 1 mM EDTA (TE buffer).

1.2. Construction of genomic DNA library of *B. laterosporus* J1

Three hundred micrograms of chromosomal DNA of *B. laterosporus* J1 was partially cleaved with 3.75 units of restriction endonuclease Sau3AI and the resultant DNA fragments were applied to 10–40% sucrose density gradient centrifugation in a rotor SRP28 (Beckman, U.S.A.) at 26,000 rpm for 20 hours. Fractions of DNA with an average size of 7–9 kilo bases (kb) were pooled and DNA was collected by ethanol precipitation and dissolved in TE buffer. The plasmid vector pHSG298 DNA (Takara Shuzo, Japan) (20 μg) was cleaved with BamHI (Takara Shuzo, Japan), followed by phenol extraction and ethanol precipitation. The DNA was dissolved in 200 μl of 10 mM Tris-HCl (pH 8) containing 10 mM EDTA and incubated at 37° C. for 20 min with 1 unit of bacterial alkaline phosphatase (Takara Shuzo, Japan). The reaction mixture was treated with phenol extraction and ethanol precipitation and dissolved in 40 μl of TE buffer. Sau3AI partially cleaved chromosomal DNA fragments of 20 μg were ligated at 12° C. for 16 hours with 500 units of T4 DNA ligase (Takara Shuzo, Japan) to 5 μg of the linearized and dephosphorylated pHSG298. The ligation mixture was used for transformation of *E. coli* JM109 (Toyobo Co., Ltd., Japan). Transformation was performed according to the procedure of O. Hanahan (Cf. J. Mol. Biol. 166, 557–580 (1983)). Except if otherwise specified, the procedure of Hanahan was adopted in all the transformation described later. The transformants were selected on LM agar containing 20 μg of Kanamycin /ml. The number of transformants was 2,000.

1.3. Selection of a clone possessing a plasmid containing a GL-7ACA acylase gene A clone possessing a plasmid containing GL-7ACA acylase gene was screened among the genomic DNA library of *B. laterosporus* J1 by the following HPLC method.

Transformant colonies were picked up and grown overnight at 30° C. in 1 ml of 2% Bouillon (Eiken Chemical Co., Ltd., Japan) supplemented with 1 mM isopropyl-β-D-galactoside (IPTG; Sigma Chemical Co., Ltd., U.S.A.). Cells were harvested by centrifugation and resulting cell pellets were used for assay. Reaction mixture (200 μl) containing 100 mM phosphate buffer (pH 8), 2 mg of GL-7ACA and cell pellets were thoroughly mixed and incubated for 10 min at 37° C. The reaction was terminated by the addition of 200 μl of 4% acetic acid. Samples were applied to a Inertsil ODS-2 column (4.6 mm × 150 mm) (Gasukuro Kogyo Co., Ltd., Japan) and elution was performed with 0.567 g/l of $Na_2HPO_4$, 0.36 g/l of $KH_2PO_4$ and 2–4% methanol. 7ACA was detected with absorption at 254 nm.

Figure 2:
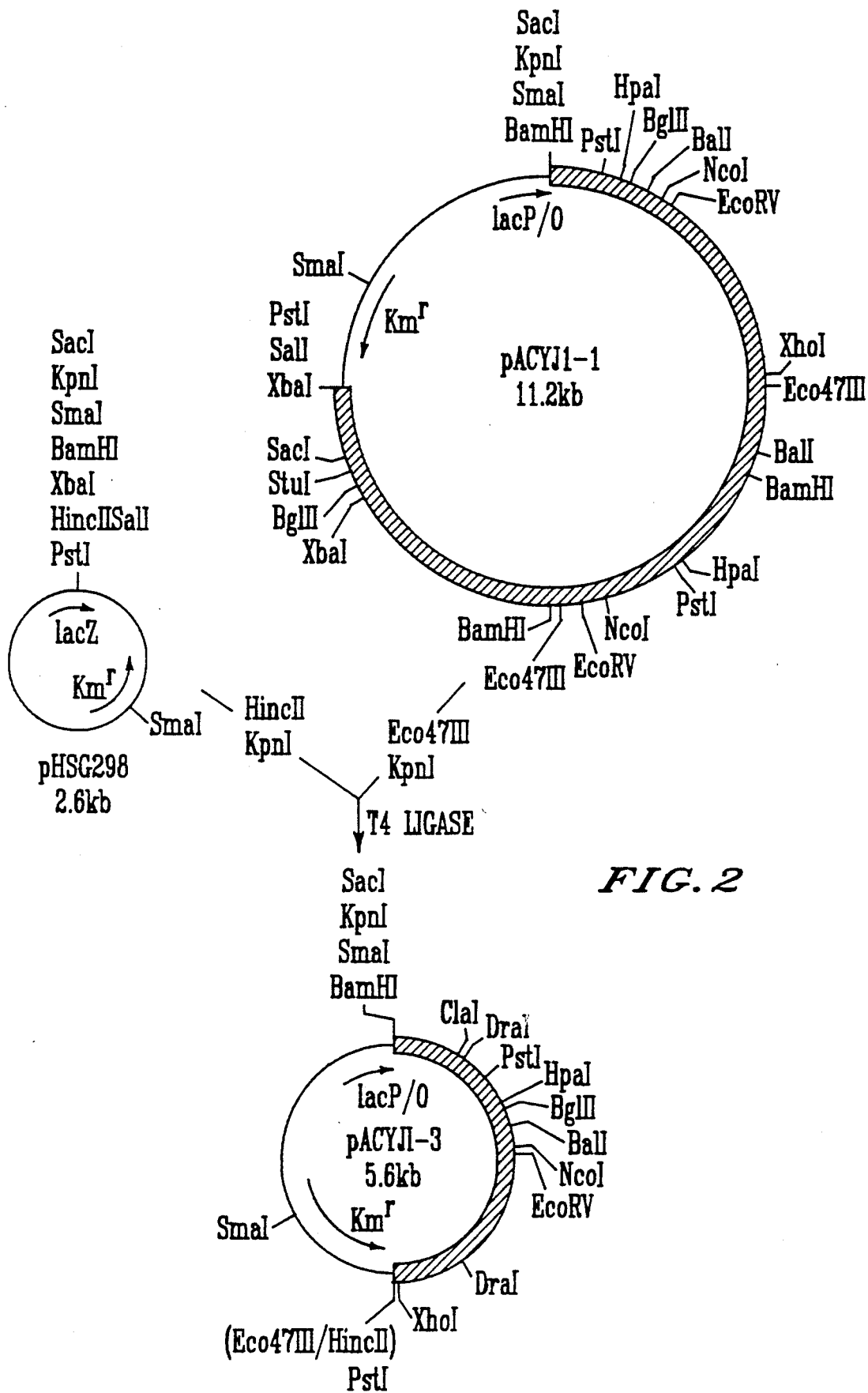
FIG. 2 shows construction and restriction cleavage map of plasmid pACYJ1-3.

1.4. Subcloning of the gene encoding GL-7ACA acylase (Cf. FIG. 1 and FIG. 2)

Plasmid DNA was extracted from the positive clone by the cleared lysate method(Cf.Clewell and Helinski, Proc. Natl. Acad. Sci., U.S.A. 62, 1159–1166, 1969) and named pACYJ1-1. The size of the insert DNA was estimated to be approximately 8.6 kb by agarose gel electrophoresis. The recombinant plasmid pACYJ1-1 DNA (10 μg) was cleaved with KpnI and Eco47III (Takara Shuzo, Japan) and the resulting DNA fragment (2.6 kb) of the insert was separated by agarose gel electrophoresis, eluted from the gel by electrophoresis, treated with phenol extraction and ethanol precipitation and dissolved in TE buffer. This DNA fragment (1 μg) of the insert was ligated with 25 units of T4 DNA ligase to 1 μg of pHSG298 DNA which was linearized by digestion with KpnI and HincII (Takara Shuzo) and isolated similarly as the insertion fragment of pACYJ-1. *E. coli* JM109 was transformed with this ligation mixture. Transformants were selected on LM agar plates containing trypton(Difco) 1%, yeast extract(Difco) 0.5%, sodium chloride 10 mM, $MgSO_4$ 10 mM, agar 1.5% and 20 μg/ml of kanamycin and confirmed by criteria of loss of β-galactosidase activity, size of an insert and presence of GL-7ACA acylase activity. Activity of GL-7ACA acylase was measured by the HPLC method as described in Example 1.3. From one of the recombinant strain, plasmid DNA was extracted by the cleared lysate method and named pACYJ1-3.

EXAMPLE 2

Determination of nucleotide sequence of the gene encoding GL-7ACA acylase of *Bacillus laterosporus J1*

2.6. Determination of nucleotide sequence

Restriction endonuclease mapping of the insert of pACYJ1-3 was performed using restriction endonucleases BalI, BglII, ClaI, DraI, EcoRV, HpaI, NcoI, PstI and XhoI (All from Takara Shuzo). Appropriate restriction endonuclease cleaved DNA fragments were subcloned into M13 phage vector and used for determination of the nucleotide sequences. Nucleotide sequence was determined by the dideoxy chain termination method (Cf. Sanger et al. Proc. Natl Acad Sci., U.S.A. 74, 5463-5467 (1977)) using M13 sequencing kit (Toyobo Co., Ltd., Japan). The enzyme used was T7 DNA polymerase (Sequenase) and 7-deaza dGTP and dITP were separately adopted as the nucleotide analog. To determine the sequence located in the middle of a long DNA fragment, one of the restriction endonuclease cleaved DNA fragment was treated with Bal31, recloned into M13 phage vector and used for sequencing. Gel electrophoresis was performed at 2200V for 5 or 13 hours using 5% polyacrylamide gel containing 7M urea of 80 cm long. The nucleotide sequence of the insert of pACYJ1-3 was shown in FIG. 4. One open reading frame of 1902 bp was recognized. This open reading frame was confirmed as the gene encoding the GL-7ACA acylase of B. laterosporus J1 by following two results. 1) The amino-terminal sequence (SEQ ID NO: 1) of GL-7ACA acylase J1 determined by gas-sequencing method (details will be described in the next Example) were identical with the amino acid sequences between codons at positions 1 and 9. This indicated that processing occurred where N-terminal peptide of 27 amino acid residues long was excised. 2) The molecular weight of 70,000 of the GL-7ACA acylase estimated by SDS-polyacrylamide gel electrophoresis was well coincided with that of 69,227 calculated from the deduced processed protein sequences for the open reading frame (details will be described later). No similarity was recognized between the amino acid sequence of GL-7ACA acylase J1 (SEQ ID NO: 3) and those of the other known cephalosporin acylases.

Figure 3:
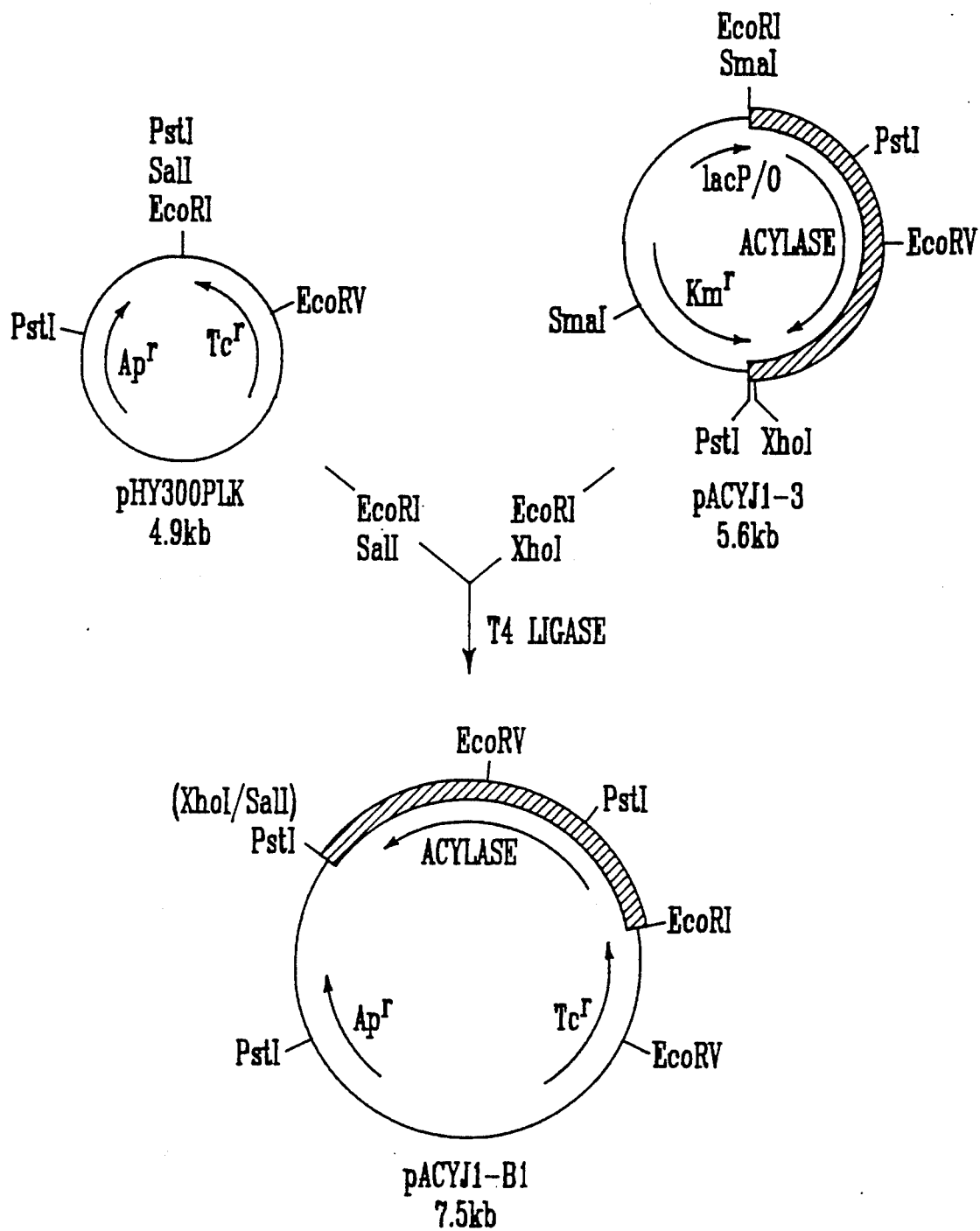
FIG. 3 shows construction and restriction cleavage map of plasmid pACYJ1-B1.

EXAMPLE 3. (Cf. FIG. 3)

Expression of the gene for GL-7ACA acylase J1 in *Bacillus subtilis*.

The recombinant plasmid pACYJ1-3 of 10 μg was cleaved with EcoRI and XhoI (Takara Shuzo) and the resulting DNA fragment of the insert of 2.6 kb which contained the structural gene for GL-7ACA acylase J1 and its own promoter and terminator was separated by agarose gel electrophoresis, eluted from the gel by electrophoresis, treated with phenol extraction and ethanol precipitation and dissolved in TE buffer. Meanwhile, and *E. coli-B.subtilis* shuttle vector named pHY300PLK (Takara Shuzo) (10 μg) was cleaved with EcoRI and SalI and the resulting DNA fragment of 4.9 kb was purified the same as described above. The purified EcoRI-XhoI cleaved fragment (1 μg) of pACYJ1-3 and EcoRI-SalI cleaved fragment (1 μg) of pHY300PLK were ligated at 12° C. for 16 hours with 25 units of T4 DNA ligase. *E coli* MC1061 was transformed with this ligation mixture Transformants were selected on LM agar plates containing 35 μg/ml ampicillin (Fujisawa Pharm. Co., Ltd.) and confirmed by criteria of size of an insert and presence of GL-7ACA acylase activity From one of the recombinant strain, plasmid DNA was extracted by the cleared lysate method and named pACYJ1-B1. *Bacillus subtilis* ISW1214 (Takara Shuzo) was transformed with this plasmid pACYJ1-B1 (1 82 g). Transformation was performed according to the procedure of C. Anagostopoulos et al (Cf. C. Anagostopoulos and J. Spizizen, J. Bacteriol. 81, 741-746 (1961)). Transformants were selected on L agar containing 20 μg/ml tetracycline. *B. subtilis* ISW1214 carrying pACYJ1-B1 which was obtained as above was grown at 30° C. for 18 hours in L broth containing 20 μg/ml tetracycline.

Supernatant and cell pellet were prepared by centrifugation of the cultured broth at 10,000 g for 20 min. GL-7ACA acylase activity in the supernatant, cell pellet and whole culture was determined by HPLC assay as described in Example 1.3. The GL-7ACA acylase activities of the supernatant, cell pellet and whole culture were 0.63, 0.04 and 0.70 unit/gram of bacteria (wet weight), respectively. Approximately 90% of GL-7ACA activity was recovered from the supernatant. Besides, it should be noted that GL-7ACA acylase activity was not detected in the whole culture of the original strain *B. laterosporus* J1 which was grown in the same manner as mentioned above and the GL-7ACA acylase activity thereof was able to be detected only when the cells were grown on agar plates.

Purification of the GL-7ACA acylase of *B. laterosporus* J1

4.1 Purification of the acylase from a recombinant *E. coli*

An aqueous medium (L broth) of 200 ml consisting 1% tryptone (Difco Laboratories, U.S.A.), 1.5% yeast extract (Difco) and 0.5% NaCl was introduced into each of five 500 ml flasks, sterilized at 121° C. for 20 min by an autoclave and supplemented with 20 μg/ml kanamycin sulfate (Meiji Seika Co., Ltd., Japan) sterilized separately by filtration. To these media was inoculated a loopful of slant culture of *E. coli* JM109 possessing pACYJ1-1, and the organism was grown at 30° C. for 24 hours with shaking at 300 rpm on a rotary shaker. Meanwhile, an aqueous medium (18 l ) comprising the same ingredients as mentioned above plus 0.04% Adecanol (Asahi Denka Co., Ltd., Japan) was introduced into a 30 l jar fermenter (Komatsugawa Co., Ltd., Japan) sterilized at 121° C. for 15 min and supplemented with 0.25 mg/ml IPTG sterilized separately by filtration. To the medium was inoculated whole volume of the cultured broth as obtained above, whereafter the organism was grown at 30° C. for 18 hours. After the completion of the culture, the cells were harvested by continuous flow centrifugation at 8,000 rpm. The cell pellet of approximately 80 g obtained was suspended in 320 ml of 0.1M phosphate buffer (pH 8) and disrupted in an ice-water bath by 5 min of sonication. The sonicated suspension was centrifuged at 8,000 g for 10 min and to the resulting supernatant, Polymin P (Bethesda Research Laboratories, U.S.A.) was added to a final concentration of 0.3%. After stirred at 4° C. for 30 min, the mixture was centrifuged at 8,000 g for 20 min. The supernatant was dialyzed against 20 mM Tris-HCl (pH 8.5). This crude extract was applied onto a column of DEAE-Toyopearl 650M (Tosoh Cooperation, Japan) (bed volume: 100 ml) which had been equilibrated with 20 mM Tris-HCl buffer (pH 8.5). After washed with the same buffer, the column was eluted with a linear gradient of NaCl (0–0.5M) in 300 ml of 20 mM Tris-HCl buffer (pH 8.5). Fractions containing GL-7ACA acylase activity were pooled and dialyzed against 20 mM Tris-HCl buffer (pH 8.5). The dialyzate was applied onto a column of DEAE-Toyopearl 650S (Tosoh Cooperation) (bed volume : 30 ml) which had been equilibrated with the same buffer. After washed with the same buffer, the column was eluted with a linear gradient of NaCl (0–0.35M) in 100 ml of 20 mM Tris-HCl buffer (pH 8.5). Active fractions were pooled and dialyzed against 50 mM phosphate buffer (pH 8.0). The dialyzate was applied onto a column of HCA 100S (Mitsui Toatsu Co., Ltd., Japan) (bed volume : 20 ml) which had been equilibrated with 50 mM phosphate buffer (pH 8.0). After washed with the same buffer, the column was eluted with a linear gradient of phosphate buffer (pH 8.0) (0.05-0.4M) (60 ml). Active fractions were pooled and dialyzed against 0.1M phosphate buffer (pH 8.0). To this dialysate, ammonium sulfate was added to make a final concentration of 35% and applied onto a column of Butyl-Toyopearl 650S (Toso Co., Ltd.) (bed volume : 20 ml) equilibrated with the same buffer containing ammonium sulfate of 35% saturation. After washed with the same buffer, the column was eluted with a linear gradient of ammonium sulfate (35-0%) in 0.1M phosphate buffer (pH 8.0). Active fractions were pooled and dialyzed against 20 mM Tris-HCl (pH 8.5). The dialysate was applied onto an HPLC column of DEAE-G (Waters Co., Ltd., U.S.A.) (0.82×7.5 cm) equilibrated with the same buffer. Elution was performed with a linear gradient of NaCl (0-0.5M) in 20 mM Tris-HCl (pH 8.5) at a flow rate of 3 ml/min over 30 min. Fractions containing GL-7ACA acylase activity were pooled and concentrated by ultrafiltration with UF-10PS filter (Tosoh Cooperation). The total quantity of the purified enzyme preparation was 9.6 mg and its purity was estimated to be 95%.

4.2 Purification of the acylase from a recombinant Bacillus subtilis

An aqueous medium (L broth) (180 ml) containing 1% tryptone (Difco Laboratories), 0.5% yeast extract (Difco) and 0.5% NaCl was introduced into each of two 500 ml flasks, sterilized at 121° C. for 20 min by an autoclave and supplemented with 20 µg/ml tetracycline (Taito-Pfizer Co., Ltd., Japan) sterilized separately by filtration. To these media was inoculated a loopful of slant culture of B. subtilis ISW1214 possessing pACYJ1-B1, respectively and the organism was grown at 30° C. for 24 hours with shaking. Meanwhile, L broth (1.8 l) was introduced into each of two 5 l flasks, sterilized at 121° C. for 20 min and supplemented with tetracycline. To each of these media was inoculated whole volume of the cultured broth as obtained above, whereafter the organism was grown at 30° C. with shaking at 300 rpm on a rotary shaker until its optical density at 600 nm came to 2.5. The cultured broth was then centifuged at 10,000 g for 20 min to remove cell pellets. The resulting supernatant (3.6 l) was dialyzed against tap water and then against 20 mM Tris-HCl (pH 8). The dialysate was applied onto a column of DEAE-Toyopearl 650M (bed volume : 100 ml) which had been equilibrated with 20 mM Tris-HCl (pH 8). After washed with the same buffer, the column was eluted with 200 mM NaCl-20 mM Tris-HCl (pH 8). Active fractions were pooled, adjusted to 60% saturation with ammonium sulfate, stirred for 30 min and centrifuged at 10,000 g for 20 min. The resulting supernatant was further adjusted to 80% saturation with ammonium sulfate, stirred and centrifuged as above. The resulting pellet was dissolved in 50 mM phosphate buffer (pH 8) containing ammonium sulfate of 45% saturation and applied onto a column of Toyopearl-HW55F (Toso Co., Ltd.) (bed volume : 30 ml). The column was eluted with ammonium sulfate of 35% saturation in 50 mM phosphate buffer (pH 8). Active fractions were pooled and dialyzed against 50 mM phosphate buffer (pH 8). The dialysate was applied onto an HPLC column of TSK gel G2000 SW (Toso Co., Ltd.) (2.15×60 cm). The column was eluted with 500 mM phosphate buffer (pH 8). Active fractions were pooled, dialyzed against 200 mM Tris-HCl (pH 8) and applied onto a column of DEAE-Toyopearl 650M (bed volume: 1 ml). The column was eluted with 200 mM NaCl-20 mM Tris-HCl (pH 8). Active fractions were pooled and dialyzed against 50 mM Tris-HCl (pH 8). The total quantity of the final enzyme preparation was 1 mg and its purity was estimated to be 93%.

EXAMPLE 5

Characterization of the GL-7ACA acylase of B. laterosporus J1 from an E. coli recombinant

5.1 Specific enzvme activity

The activity of the GL-7ACA acylase J1 was determined by HPLC assay. Reaction mixture (200 µl) containing (a) 100 mM glycine buffer (pH 9), 1.4-20 mM GL-7ACA and 11 µg of enzyme or (b) 100 mM Tris-HCl buffer (pH 8), 0.16-5 mM GL-7ACA and 5 µg of the enzyme was used. R mixtures were incubated for 2 min at 37° C. and the reaction was terminated by addition of 200 µl of 4% acetic acid. Conditions for HPLC were the same as those described in Example 1.3. All assays used later in this section was HPLC method. Specific enzyme activity was expressed as unit per mg of protein. Protein concentrations were determined by Bio-Rad protein assay kit (Bio-Rad Co., Ltd., U.S.A.) with bovine serum albumin as a standard. Maximum specific enzyme activity (Vmax) and Michaelis constant (Km) were calculated from slope and intersection which were obtained by Lineweaver-Burk plot (Cf. M. Dixon and E. C. Webb, Enzymes, Longmans, London, 1958). Maximum specific enzyme activity of GL-7ACA acylase J1 in glycine buffer (pH 9) was 5.3 units/mg and that in Tris-HCl buffer (pH 8) was 4.8 units/mg. Km values of GL-7ACA acylase J1 in glycine buffer (pH 9) was 3.2 mM and that in Tris-HCl buffer (pH 8) was 0.14 mM.

5.2. Substrate profile

Enzyme activity was determined by HPLC assay. Reaction mixture (200 µl) containing 20 µmol of Tris-HCl buffer (pH 8), 2 mg of a substrate and 22 µg of the enzyme was used. The reaction mixture was incubated at 37° C. for 2 min and the reaction was terminated by addition of 4% acetic acid. The relative enzyme activity was expressed as a percentage compared to the activity for GL-7ACA. The result was shown in Table 3.

TABLE 3

| Substrate profile of GL-7ACA acylase J1. | |
|---|---|
| Substrates | Relative enzyme activity |
| Succinyl 7ACA | 6.1 |
| Glutaryl 7ACA | 100 |
| Adipyl 7ACA | 68 |
| D-Glutamyl 7ACA | 0.55 |
| Cephalosporin C | N.D. |
| N-Acetyl Cephalosporin C | N.D. |
| Cephalothin | N.D. |

N.D. (not detected)

Figure 5:
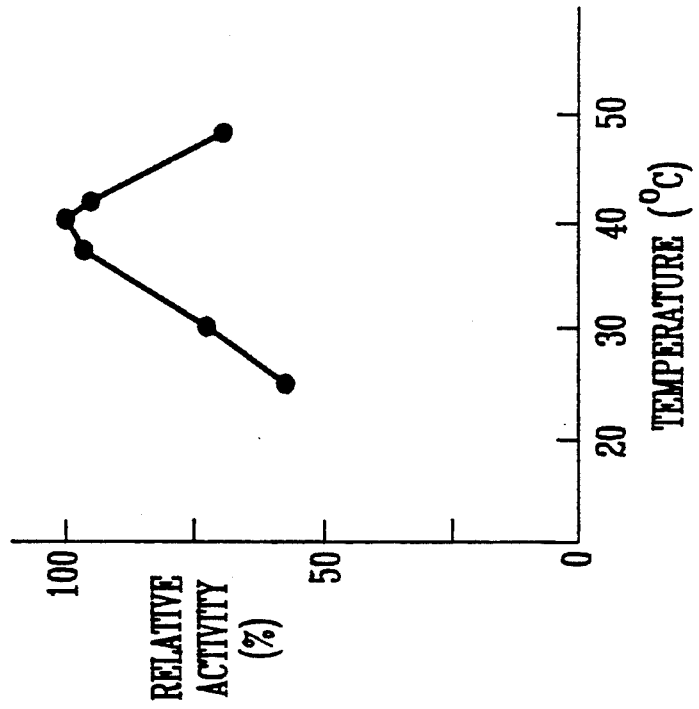
FIG. 5 shows optimum temperature of the GL-7ACA acylase J1.

5.3. Effect of temperature a) Optimum temperature (Cf. FIG. 5)

Reaction mixture (200 µl) containing 20 µmol of Tris-HCl buffer (pH 8), 0.4 mg of GL-7ACA and 22 µg of the enzyme was used. Reactions were performed for 2 min at various temperatures from 25° to 50° C. The optimum temperature was 40° C.

b) Termostability

23 μg/ml of partially purified GL-7ACA acylase J1 (purity 16%) was treated at 45° C. for 2 hours in 0.1M phosphate buffer (pH 8) and the residual enzyme activities were assayed in the reaction mixture containing 0.1M Tris-HCl buffer (pH 8), 2 mg/ml of GL-7ACA and 2.3 μg/ml of the treated enzyme. Reaction was performed at 37° C. for 2 min.

Figure 6:
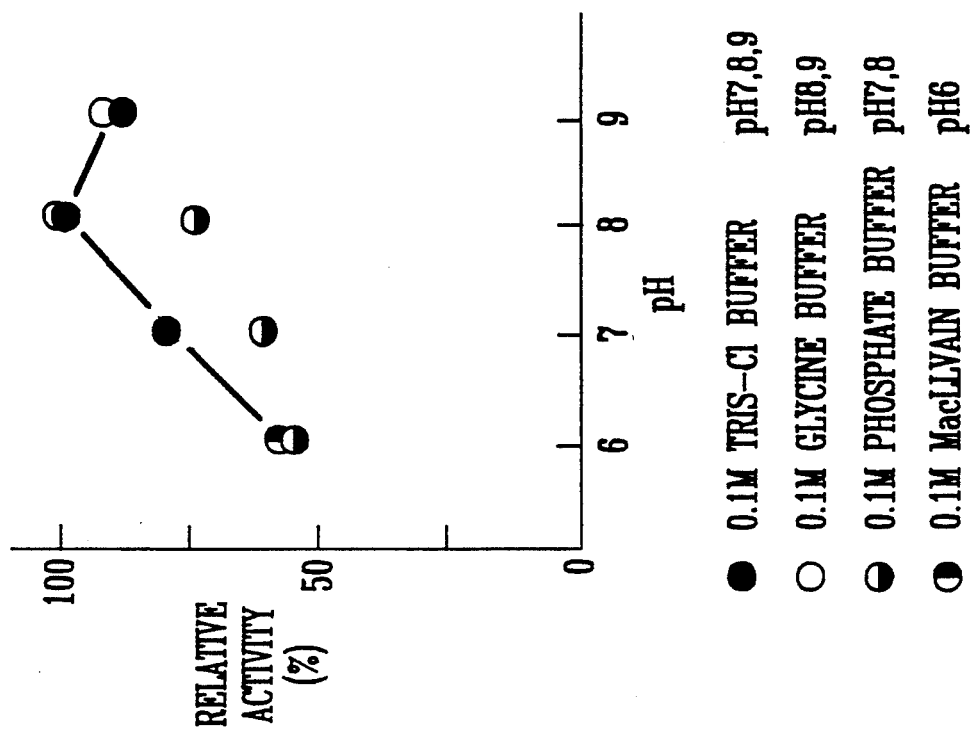
FIG. 6 shows optimum pH of the GL-7ACA acylase J1.

5.4. Effect of pH.

a) Optimum pH. (Cf. FIG. 6)

Figure 7:
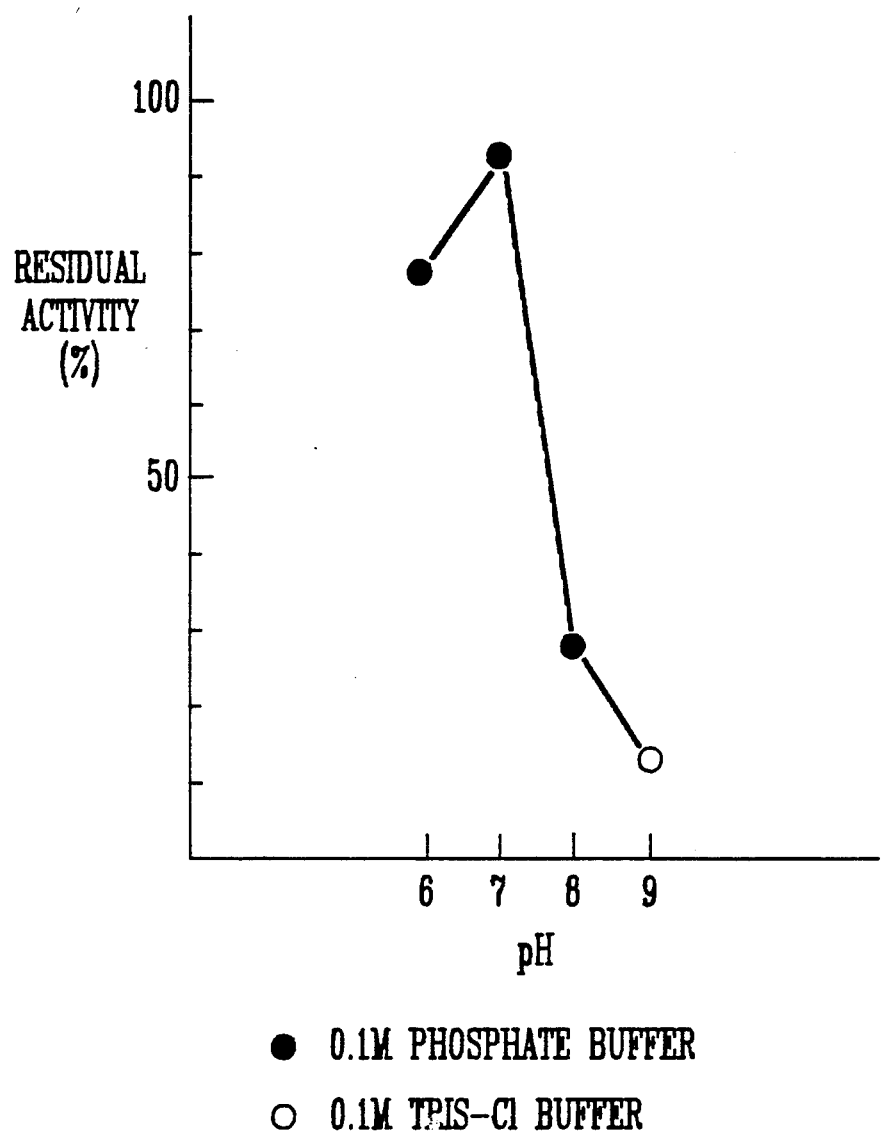
FIG. 7 shows pH profile of stability of the GL-7ACA acylase J1.

Reaction mixture (200 μl) containing 20 μmol of buffer (MacIlvain buffer used at pH 6, phosphate buffer used between pH 6–8, Tris-HCl buffer between pH 7–9 and glycine buffer between pH 8–9), 0.4 mg of GL-7ACA and 22 μg of the enzyme was used. Reaction was performed at 37° C. for 10 min. Optimum pH for GL-7ACA acylase J1 was 8.

b) pH profile of stability. (Cf. FIG. 7)

One hundred μg/ml of GL-7ACA acylase J1 was treated at 50° C. for 1 hour in 0.1M buffer of various pH (phosphate buffer used for pH 6, 7 and 8 and Tris-HCl buffer used at pH 9). The residual enzyme activity was assayed in the reaction mixture (200 μl) containing 20 μmol of phosphate buffer (pH 8), 0.4 mg of GL-7ACA and 2 μg of the treated enzyme. Reaction was performed at 37° C. for 10 min.

1 5.5. Inhibition by reaction products a) Effect of reaction products on the enzyme activity of GL-7ACA acylase J1

Inhibitory activity of reaction products, namely 7-ACA and glutaric acid on the enzyme activity of GL-7ACA acylase J1 was examined. The enzyme activity was assayed in the presence of various concentrations of 7-ACA or glutaric acid. For determination of Ki of 7-ACA, reaction mixture (200 μl) containing 20 μmole of glycine buffer (pH 9), 0.39–2.0 μmole of GL-7ACA, 0.3–0.48 μmole of 7-ACA and 11 μg of enzyme was used and the reaction was performed at 37° C. for 6 min. For determination of Ki of glutaric acid, reaction mixture (200 μl) containing (a) 20 μmole of glycine buffer (pH 9), 0.26–3.0 μmol of GL-7ACA, 2–10 μmol of glutaric acid and 11 μg of the enzyme (b) 20 μmol of Tris-HCl buffer (pH 8), 0.05–1.0 μmol of GL-7ACA, 0.25–0.1 μmol of glutaric acid and 5 μg of the enzyme was used. The reaction was performed at 37° C. for 3 min. Lineweaver-Burk plots in the absence and presence of both inhibitors were shown to possess the same intersection at vertical axis, indicating that mode of inhibition by both inhibitors was competitive. Ki values were calculated from the apparent Michaelis constants (Kmapp), Km and Vmax. Ki values of 7-ACA was 2.0 mM. Ki value of glutaric acid in the reaction using 0.1M glycine buffer (pH 9) was 53 mM whereas that in the reaction using 0.1M Tris-HCl buffer (pH 8) was 0.99 mM.

b) Effect of various enzyme inhibitors.

Effect of p-chloromercuribenzoate (pCMB, Sigma Chemical Co., Ltd.), phenylmethylsulfonyl fluoride (PMSF, Sigma) and ethylenediaminetetraacetic acid (EDTA, Nacalai Tesque Inc., Japan) on the activity of GL-7ACA acylase J1 was examined as follows. Eleven μg of GL-7ACA acylase J1 was treated at 37° C. for 3 hours with 1.0 or 5.0 mM pCMB, 1.0 or 5.0 mM PMSF, or 1.0 or 5.0 mM EDTA in 200 μl of 0.1 M Tris-HCl buffer (pH 8). Residual activity of the treated enzyme was assayed by adding 22 μl of GL-7ACA (20 mg/ml) as a substrate to the mixture. The reaction was performed at 37° C for 10 min. Residual activity was expressed as a percentage compared to the activity of the enzyme treated with blank solution. The results are shown in the following Table 4.

TABLE 4

Effect of inhibitors on acylase activity of GL-7ACA acylase J1

| Inhibitor (mM) | Relative activity (%) |
|---|---|
| None | 100 |
| EDTA(1 mM) | 100 |
| EDTA(5 mM) | 102 |
| PMSF(1 mM) | 90 |
| PMSF(5 mM) | 78 |
| pCMB(1 mM) | 106 |
| pCMB(5 mM) | 104 |

5.6. Determination of isoelectric point (pI)

Analytical isoelectric focusing of GL-7ACA acylase J1 was performed according to the method of Olsson et al (Cf. B. Olsson, C. E. Nord, T. Wadstrom and B. Wretlind, FEMS Microbiol. Lett. 1. 157–162 (1977)). The preparations of GL-7ACA acylase J1 purified from recombinant strains of *E coli* and *B. subtilis* were applied on thin layer of 4% polyacrylamide gel containing 2% Ampholine pH range 3.5–10 (Pharmacia LKB Biotechnology, Sweden). The proteins were electrofocused for 2 hours at 100 volts using isoelectric focusing apparatus SJ-1071EC (ATTO Co., Ltd., Japan). After electrofocusing, the gel was stained with Coomassie Brilliant Blue R-250 and the isoelectric point was determined from the calibration curve made with pI markers (Pharmacia LKB Technology) which were run simultaneously with the sample. The pI values of the preparations of GL-7ACA acylase J1 purified from recombinant strains of *E. coli* and *B. subtilis* were identical and estimated to be 4.7.

5.7 Determination of molecular weight by SDS-polyacrylamide gel electrophoresis Sodium dodecyl sulfate (SDS)-polyacrylamide gel electrophoresis was performed by the procedure described by Laemmli (Cf. U. K. Laemmli; Nature 237, 680–685 (1970)). Egg white lysozyme (molecular weight 14,000), soybean trypsin inhibitor (21,000), bovine carbonic anhydrase (31,000), egg white ovalbumin (43,000), bovine serum albumin (68,000), rabbit muscle phosphorylase b (97,000) were purchased from Bio-Rad Laboratories and used as molecular weight standards The final preparation of GL-7ACA acylase J1 purified from either a recombinant *E. coli* or a recombinant *B. subtilis* showed one homogeneous band on SDS-gel electrophoresis. The molecular weights of the two GL-7ACA acylase J1 preparations were identical and calculated to be 70,000.

5.8. Determination of amino acid sequence

The preparations of GL-7ACA acylase J1 purified from recombinant strains of *E. coli* and *B. subtilis* were denatured by its incubation at 37° C. for 30 min in 8M urea and then applied to a reversed phase HPLC. Column used was Cosmosil 5C4-300 (4.6 mm × 5 cm, Nacalai tesque). Elution was performed with a linear gradient of acetonitrile (30% to 60%) in 0.1% trifluoroacetic acid at a flow rate of 1 ml/min over 20 min. The amino acid sequences of the two preparations of J1 acylase were determined by a gas-phase sequencer 470A (Applied Biosystems, U.S.A.). The N-terminal amino acid sequences of the two preparations were identical and were Gln-Ser-Glu-Gln-Glu-Lys-Ala-Glu-Glu (SEQ ID NO: 1).

The newly isolated Bacillus laterosporus J1 and the transformants as mentioined below in which expression plasmids obtained in the above Example were inserted, have been deposited with one of the INTERNATIONAL DEPOSITORY AUTHORITY ON THE BUDAPEST TREATY, Fermentation Research Institute (FRI), Agency of Industrial Science and Technology at 1-3, Higashi 1 chome, Tsukubashi, Ibaraki-ken 305, Japan on Sep. 18, 1990.

| Organism | Deposit number |
| --- | --- |
| *Bacillus laterosporus* J1 | FERM BP-3106 |
| *Escherichia coli* JM109 (pACYJ1-3) | FERM BP-3105 |
| *Bacillus subtilis* ISW1214 (pACYJ1-B1) | FERM BP-3107 |

We claim:

1. An isolated and purified 7-(4carboxybutanamido)-3-acetoxymethyl-3-cephem-4-carboxylic acid (GL-7-ACA) acylase having the following characteristics:
   (a) catalyzes the enzymatic conversion of glutaryl 7 aminocephalosporic acid (7-ACA), adipyl 7-ACA, and succinyl 7-ACA, into 7-aminocephalosporanic acid,
   (b) has a molecular weight of 70,000 daltons (SDS-PAGE)
   (c) has an N-terminal amino acid sequence (SEQ ID NO: 1) of the formula:

Gln-Ser-Glu-Gln-Glu-Lys-Ala-Glu-Glu SEQ ID NO. 1 and
   (d) is derived from Bacillus laterosporus J1.

2. The GL-7ACA acylase of claim 1 which consists essentially of the amino acid sequence 1–607 SEQ ID NO. 2.

3. A process for preparing a compound of the formula (I):

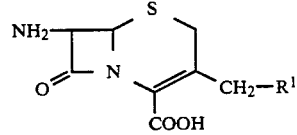

wherein $R^1$ is acetoxy, hydroxy or hydrogen, or a salt thereof,
which comprises contacting a compound of the formula (II):

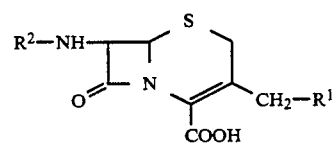

wherein
  $R^1$ is the same as defined above,
  $R^2$ is carboxy ($C_1$-$C_6$) alkanoyl, or D-glutamyl, or a salt thereof
with the cultured broth of a transformant transformed by an expression vector comprising a DNA sequence which encodes the GL-7ACA acylase of claim 1 or 2 or its processed material.

4. The process of claim 3, wherein said transformant is a cell of the species *Escherichia coli* or *Bacillus subtilis*.

* * * * *